United States Patent
Salani et al.

(10) Patent No.: US 7,445,142 B2
(45) Date of Patent: Nov. 4, 2008

(54) DEVICE FOR STORING AND DISPENSING ITEMS

(76) Inventors: Theodore R. Salani, 7721 Dalewood Pkwy., Woodridge, IL (US) 60517; Lawrence Salani, 604 Geri Ct., Palatine, IL (US) 60067

(\*) Notice: Subject to any disclaimer, the term of this patent is extended or adjusted under 35 U.S.C. 154(b) by 643 days.

(21) Appl. No.: 10/863,141

(22) Filed: Jun. 7, 2004

(65) Prior Publication Data
US 2005/0017059 A1    Jan. 27, 2005

Related U.S. Application Data

(60) Provisional application No. 60/476,657, filed on Jun. 6, 2003, provisional application No. 60/524,606, filed on Nov. 24, 2003.

(51) Int. Cl.
*B65D 27/08* (2006.01)
*B65D 27/22* (2006.01)
(52) U.S. Cl. .......................... 229/72; 229/84; 206/102; 206/441
(58) Field of Classification Search ............ 229/72, 229/84; 206/96, 102, 441, 472, 476
See application file for complete search history.

(56) References Cited

U.S. PATENT DOCUMENTS

| | | | | | |
|---|---|---|---|---|---|
| 2,035,196 | A | * | 3/1936 | Schiek | 206/441 |
| 2,139,291 | A | * | 12/1938 | Topjian | 422/126 |
| 2,201,771 | A | * | 5/1940 | Hagelauer | 131/251 |
| 2,350,144 | A | * | 5/1944 | Barros | 206/112 |
| D138,698 | S | * | 9/1944 | Salfisberg | D9/701 |
| 2,547,779 | A | * | 4/1951 | Renyck | 206/229 |
| 2,823,798 | A | * | 2/1958 | Volckening et al. | 229/221 |
| 3,720,304 | A | * | 3/1973 | Laugherty et al. | 118/31.5 |
| 4,006,819 | A | * | 2/1977 | Elliott | 206/104 |
| 4,081,076 | A | * | 3/1978 | Eisele | 206/106 |
| 4,917,236 | A | * | 4/1990 | Galvez-Moran | 206/102 |
| 5,470,323 | A | * | 11/1995 | Smith et al. | 604/289 |
| 6,124,522 | A | * | 9/2000 | Schroeder | 602/57 |

OTHER PUBLICATIONS

Two photographs and two drawings depicting side views of a device entitled "Quick Pack".

\* cited by examiner

*Primary Examiner*—Nathan J Newhouse
*Assistant Examiner*—Jack H Morgan, Jr.
(74) *Attorney, Agent, or Firm*—Marshall, Gerstein & Borun LLP

(57) ABSTRACT

A device for storing and dispensing items comprises a first item container having a main body and a tail extending from the main body, a first panel, a second panel connected to the first panel along a first fold line, and a third panel connected to the second panel along a second fold line. The second panel and the third panel defining a pocket with at least a portion of the tail being disposed in and connected to the pocket. The pocket is foldable along the first fold line to a closed position in which the main body, the third panel, the tail, and the second panel overlie the first panel, and the pocket is further foldable to an open position in which the third panel, the tail, and the second panel are angled away from the back panel.

14 Claims, 3 Drawing Sheets

DEVICE FOR STORING AND DISPENSING ITEMS

CROSS REFERENCE TO RELATED APPLICATIONS

This application claims priority from U.S. Provisional Application No. 60/524,606, filed Nov. 24, 2003, and U.S. Provisional Application No. 60/476,657, filed Jun. 6, 2003, the entire disclosures of which are incorporated by reference herein.

FIELD OF THE INVENTION

The present invention relates generally to a method and device for conveniently packaging, storing, and/or dispensing items.

BACKGROUND OF THE INVENTION

Medical devices such as adhesive bandage strips are generally are sold in sterile, individual packaging. A plurality of the adhesive bandage strips are then typically disposed in a box for transport and ultimate sale. For example, a box typically contains 10-50 individually wrapped adhesive bandages.

Unfortunately, many people find it cumbersome to pull out an individual bandage, especially if that person is injured or otherwise has limited dexterity. Further, many bandages are packaged with a variety of sizes in the box, and thus it can be especially difficult for the user to find and grasp the desired size.

The so-called "matchbook" design has been used to dispense adhesive bandages. In the matchbook design, the individual bandages are stored in a manner similar to the matches are stored in a conventional matchbook. However, the matchbook design may, in at least some applications, present drawbacks.

Figure 1:
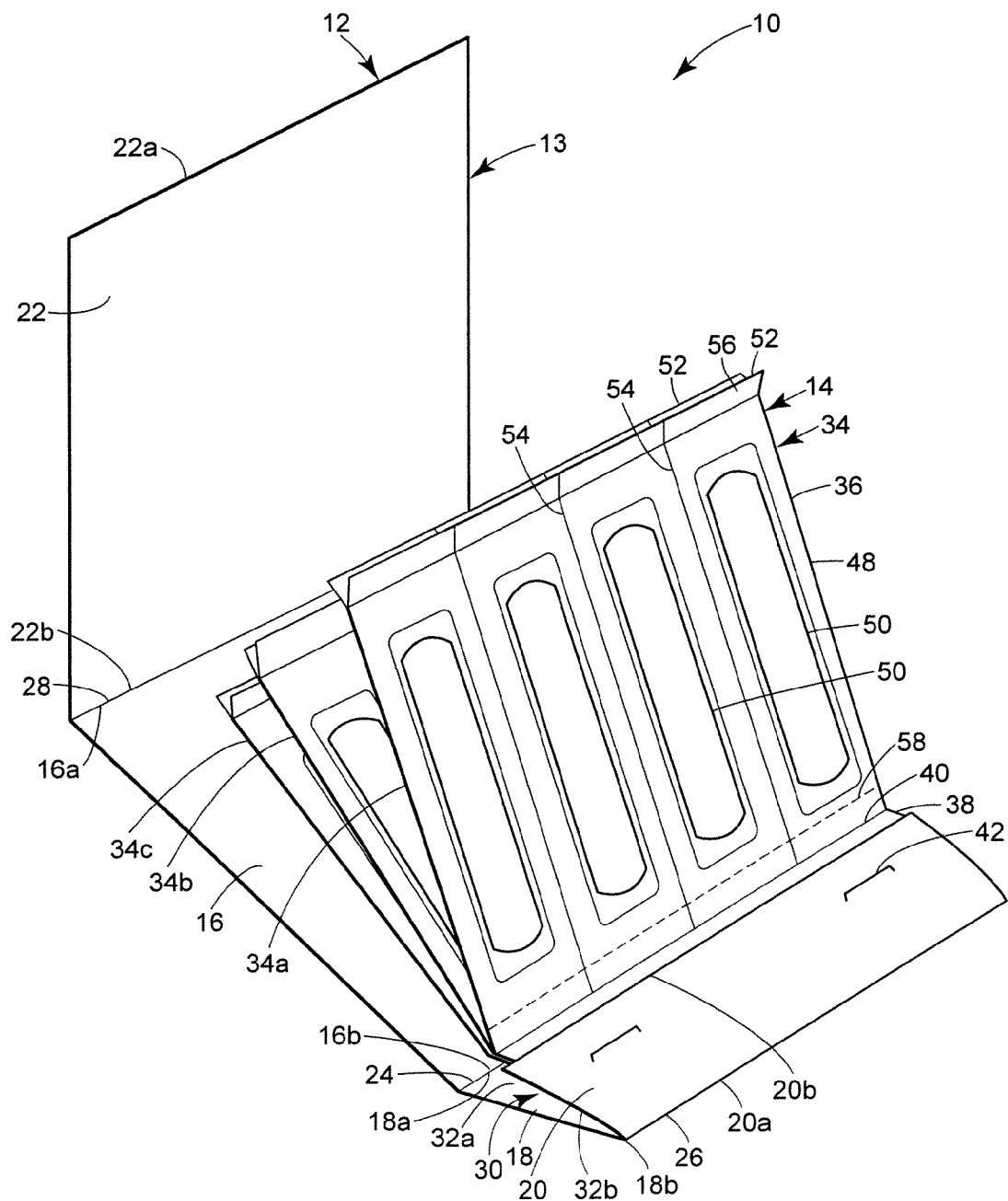
FIG. 1 is a perspective view of a device for storing and dispensing items constructed in accordance with the teachings of the present invention and showing the device in an open or partially open position.

While the invention is susceptible to various modifications and alternative constructions, certain illustrative embodiments of the invention have been shown in the drawings and will be described below in detail. It should be understood, however, that there is no intention to limit the scope of the invention to the specific form or forms disclosed. Instead, the intention is to cover all modifications and alternative constructions, as well as their equivalents, falling within the spirit and scope of the invention as defined by the appended claims.

DETAILED DESCRIPTION

Referring now to FIG. 1 of the drawings, a device for storing and dispensing items assembled in accordance with the teachings of the present invention is shown and is generally referred to by the reference numeral 10. The device 10 includes a panel assembly 12 and is preferably used to store and/or dispense one or more items which, in the disclosed example, take the form of a storage assembly 14. The panel assembly 12 includes a plurality of panels separated by fold lines and, in the example shown, preferably includes a first panel 16, a second panel 18, a third panel 20, and a fourth panel 22. The item container 34 preferably includes a main body 36 and a tail 38 connected to the main body 36 along a fold line 40. In the example shown, the second and third panels 18 and 20 are folded along a fold line to form a pocket 30, and the tail 38 is disposed in and preferably within the pocket 30.

Preferably, the first panel 16 includes a first edge 16a and a second edge 16b, the second panel 18 includes a first edge 18a and a second edge 18b, the third panel 20 includes a first edge 20a and a second edge 20b, and the fourth panel 22 includes a first edge 22a and a second edge 22b. Still preferably, the second edge 16b of the first panel 16 meets the first edge 18a of the second panel 18 along a first fold line 24. Similarly, the second edge 18b of the second panel 18 meets the first edge 20a of the third panel 20 along a second fold line 26, and the first edge 16a of the first panel 16 meets the second edge 22b of the fourth panel 22 to along a third fold line 28.

In accordance with the disclosed example, the third panel 20 may be folded along the fold line 26 to a position in which the panel 20 cooperates with at least a portion of the panel 18 to define a receiving area or pocket 30. More specifically, a surface 32b of the panel 20 generally faces a surface 32a of the panel 18. Preferably, the panels 18 and 20 may be held in the position shown in FIG. 1 using a fastener 42. The fastener 42 may be, by way of example rather than limitation, a mechanical fastener such as a staple, a bent wire, a snap, a button, or any other form of mechanical fastener, an adhesive, a hook and loop closure, or any other suitable structure for maintaining the panels 18 and 20 generally in the relationship as shown in FIG. 1. Preferably, as will be explained in greater detail below, the pocket 30 is generally sized to receive the tail portion 38 of the storage assembly 30.

The panel assembly 12 can be manufactured out of any material that is relatively lightweight and somewhat durable, such as plastic or paperboard. In this example, the panel assembly 12 is constructed from a single paperboard blank 13 which may be readily die cut and/or otherwise conveniently formed. The blank 13 can be scored along the fold lines 24, 26, 28 to improve the ease with which the blank can be folded about the fold lines 24, 26, 28. In another example, the panels 16, 18, 20, 22 can be created separately, then connected along the fold lines 24, 26, 28 using hinges, tapes, or any other suitable structure or method. Still other materials and/or methods of manufacture may be contemplated.

The storage assembly 14 includes a plurality of item containers 34. In this example, a total of three item containers 34 are depicted, however, the storage assembly 14 can include more or fewer item containers 34. In this example, the first item container 34a is shorter than the second item container 34b, so as to make it easier to separate the first item container 34a from the second item container 34b. Aside from the height, each item container 34 may be similar. For purposes of brevity, only a single one of the item containers 34 need be described in detail herein. However, it will also be understood that the items and/or the individual item containers need not be similar.

The item container 34 includes the main body 36 and the tail 38 connected along the fold line 40. The tail 38 is disposed in the pocket 30 and is connected to the panel assembly 12 either by connecting the tail 38 to the panel 18 and/or by connecting the tail 38 to the panel 20. As stated above, the tail 38 of the item container 34 is fastened to the panel assembly 12 using a pair of the fasteners 42 which, in the disclosed example, extend through both the panel 18 and the panel 20. Again, other structures may prove suitable such as, by way of example rather than limitation, adhesives, rivets, screws, snaps, buttons, hook and loop closures, etc.

The item container 34 includes a front sheet 44 and a rear sheet 46. In the disclosed example, the front sheet 44 and the rear sheet 46 are preferably adhered together using an adhesive. Still preferably, a storage receptacle 48 is defined between the front sheet 44 and the rear sheet 46. In at least one preferred form of use, the receptacles 48 may be completely sealed from the environment.

An item 50 can be stored in each receptacle 48. In the present example, medical devices are stored in each of receptacles 48. Moreover, in the example shown in FIG. 1, each item 50 is individually wrapped and is thus separated from its next adjacent item. Further, in accordance with the disclosed example, the item 50 stored within the receptacle 48 may be an adhesive bandage, a disposable thermometer, or any other item including non-medical items that may benefit from the type of storing and dispensing device 10 discussed herein.

In further accordance with the disclosed example, a top edge 36a of the main body 36 may include a pair of tabs 52. Preferably, the pair of tabs 52 can be used to easily pull the front sheet 44 away from the rear sheet 46, in order to provide convenient access to the item 50 stored within the receptacle 48.

The item container 34 can further include cuts 54 in between the items 50 to define a plurality of strips 56, such that each strip 56 includes a receptacle 48 and an item 50. The cuts 54 can be substantially perpendicular to the fold line 40 as shown in FIG. 1, but need not be. The cuts 54 can be such that the strips 56 are completely separated from the other strips 56 by the cuts 54. The cuts 54 can also be perforations to define a frangible connection such that each strip 56 is not completely separate from the adjacent strip 56, but the strips 56 can easily be separated by pulling them apart.

Further, a second frangible connection 58 can be disposed substantially parallel to the item container fold line 40 to allow each individual strip 56 to be removed from the container 10. The second frangible connection can be a perforation line, as is known.

Figure 2:
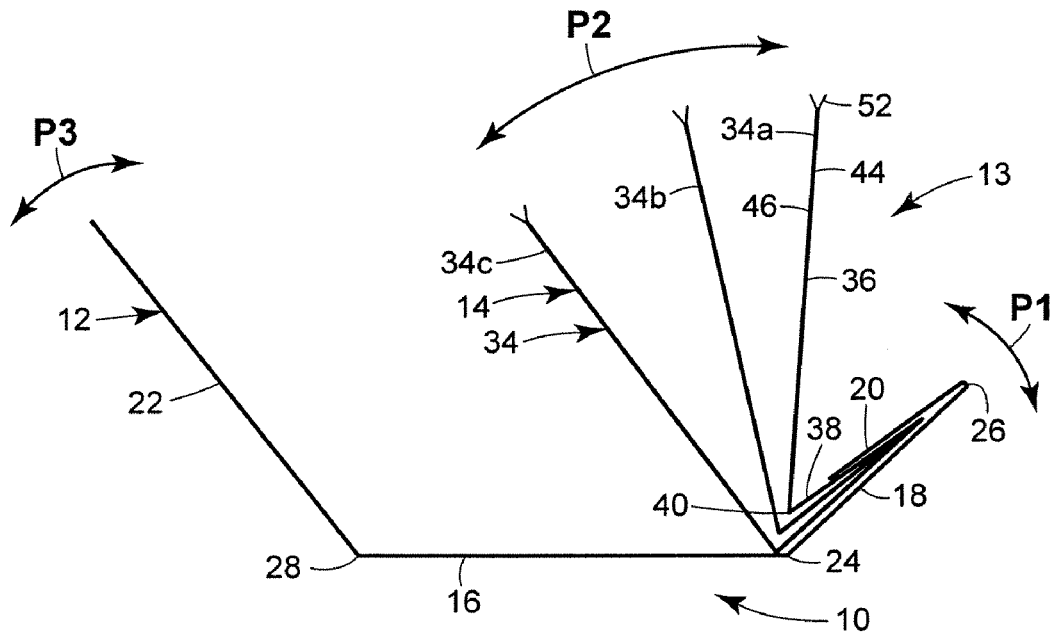
FIG. 2 is a side view of the device in an open or partially open position.

Referring now to FIG. 2, the container 10 is depicted in an open position. In the open position, the second panel 18, the third panel 20, and the tail 38 are folded away from the first panel 16 through a first arcuate path P1 about the first fold line 24. Further, the main body 36 can be folded away from both the first panel 16 as well as the second panel 18, the third panel 20 and the tail 38 through a second arcuate path P2, about the item container fold line 40. In this example, the first, second and third item containers 34a, 34b, 34c can fan out to be angled apart from each other to ease the grasping of an individual item container 34. Finally, in the open position, the fourth panel 22 is folded away from the first panel 16 through a third arcuate path P3 about the third fold line 28.

Figure 3:
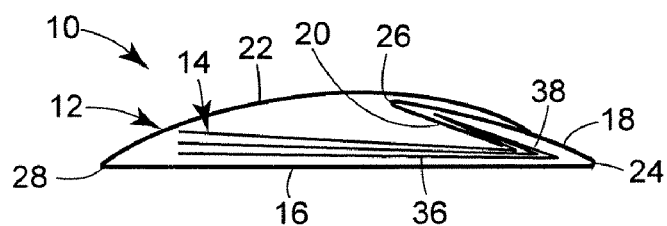
FIG. 3 is a side view of the device in a closed position.

Referring now to FIG. 3, the container 10 is depicted in a closed position. It will be noted that, for purposes of clarity, the vertical dimensions when viewing FIG. 3 has been exaggerated slightly. As shown, a portion of the main body 36 of the storage container 34 is disposed between the panels 16 and 22, while another portion of the main body 36 is disposed between the panel 20 in the panel 16. As outlined above, the tail 38 is disposed in the pocket 30 between the panels 18 and 20. The second panel 18, the third panel 20, and the tail 38 are disposed over the main body 36. Finally, the fourth panel 22 is disposed over the second panel 18.

Figure 4:
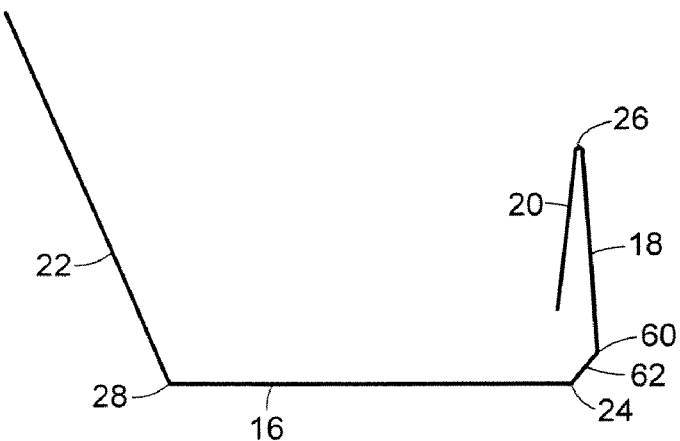
FIG. 4 is a side view of one example of a paperboard blank that can be used to form the device.

Referring now to FIG. 4, an alternative example of the panel assembly 12 is shown. In this example, a spacer panel 62 is defined between the panel 16 and the panel 20. The spacer panel 62 is separated from the panel 18 fold line 60, and is separated from the panel 16 at the fold line 24. In accordance with the disclosed example, the spacer panel 62 provides extra room between the panel 20 in the panel 16 (when the device 10 is situated as shown in FIG. 3), and therefore accommodates thicker items. Still further, any one of the other fold lines 26 or 28 may be similarly modified to include any spacer panel as desired.

Figure 5:
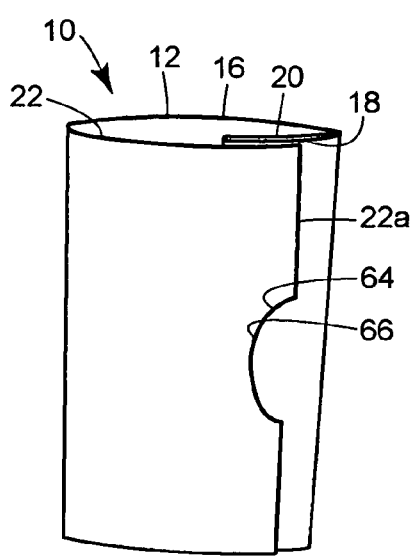
FIGS. 5-8 depict an exemplary sequence of opening the device to access the items stored therein.
Figure 6:
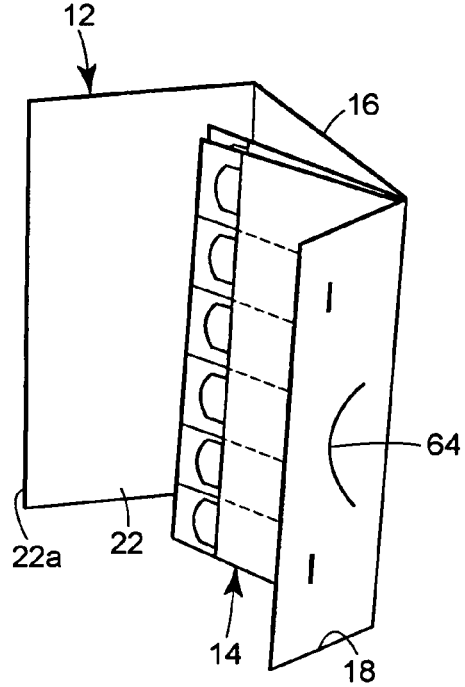
Figure 7:
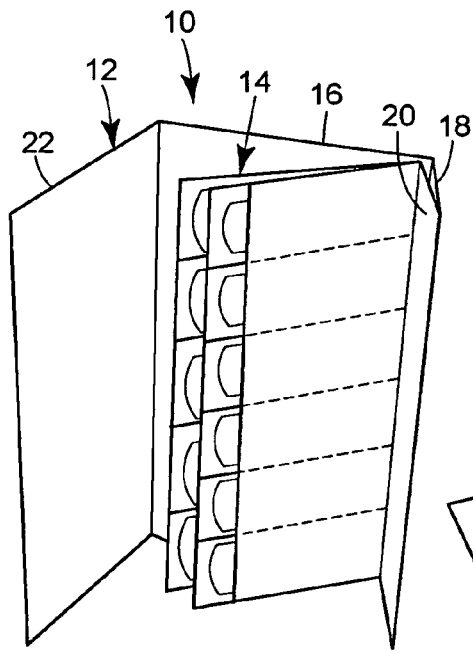
Figure 8:
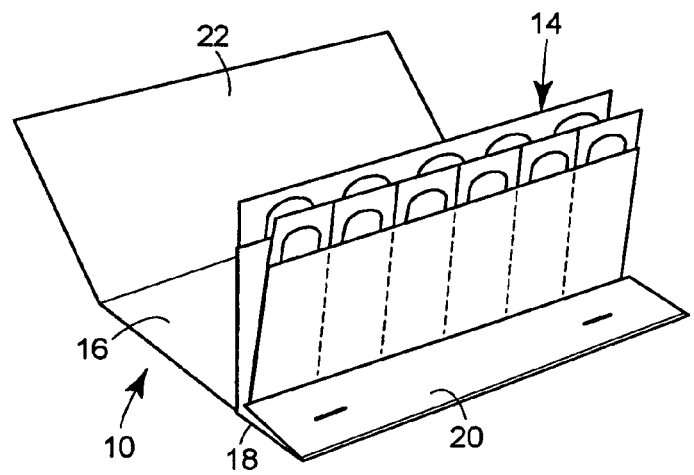

Referring now to FIGS. 5-8, an exemplary sequence is shown in which the container 10 is shifted from the closed position of FIG. 5, toward the open position of FIG. 8. In this exemplary sequence of operation, the panels 18 and 20 which include the pocket 30 formed between the panels 18 and 20, are folded or pivoted in conjunction about the fold line 24 that separates the panel 18 from the panel 16. As outlined above, the tail 38 of the item container is disposed within the pocket 30. When the panels 18 and 20 are pivoted in conjunction as shown, the main body 36 of the item containers tends to be pulled away from the surface of the panel 16. The user (not shown) may manipulate the two panels 18 and 20 relative to the panel 16 until the storage assembly 14 is positioned in a desired position disposed away from the panel 16, with at least one such desired position being shown in FIG. 8. When positioned as shown in FIG. 8, or in any other desired position in which the assembly 14 is conveniently spaced away from the surface of the panel 16, the user may conveniently grasp an individual one of the items.

As shown in FIGS. 5 and 6, the second panel 18 can include a semi-circular cut 64 to define a semi-circular flap 66. The first edge 22a of the fourth panel 22 can advantageously be tucked into the flap 66 to maintain the panel assembly 12 in the closed position. Other suitable structure can be used to releasably maintain the panel assembly 12 in the closed position, such as hook and loop fasteners, snaps, releasable adhesives, mechanical fasteners, or any other suitable structures.

To place the container 10 in the open position, the fourth panel 22 is removed from the flap 66 and folded about the third fold line 28 away from the first panel 16. See FIG. 6. The pocket 30 is then folded about the first fold line 24 away from the first panel 16, as shown in FIG. 7, until the container is in the open position depicted in FIG. 8. In the open position, the item containers 34 can be constructed such that the main bodies 36 flip away from the first panel 16. This can be accomplished by choosing a material for the sheets with sufficient resiliency that the main body 36 will not simply lay against the first panel 16 but will instead pivot upward about the item container fold lines 40. Further, the individual item containers 34a and 34b can be selected with differing levels of resiliency such that in the open position the item containers 34a and 34b are angled away from each other or fan out (see FIG. 2). In accordance with the disclosed example, the items can be disposed away from the surface of the panel 16 without bending the panel 16.

In other examples, medical devices other than individually wrapped adhesive bandages may be stored in the device 10. For example, these other items may include, by way of example rather than limitation, disposable thermometers, tongue depressors, scalpels, swabs, bandages, condoms, individually-packaged doses of medication, toothpicks, etc. Further, other implements can be stored that are not even in the medical field. In short, pockets can be formed that have any shape, size or configuration to store any item therein.

Other methods and structure can easily be designed to create a pocket bore a sealed pocket for an item. For example, instead of two sheets that are adhesively connected, individual flexible tubes or bags could be employed that define a sealed receptacle and are fastened in the pocket 30. In other examples, the receptacles 48 are not necessarily long and narrow. The receptacles can be wide, depending on the device to be contained.

This configuration using four panels 16, 18, 20, 22 foldably connected along fold lines 24, 26, 28 may result in a package having smaller folded (closed) size than that presently available in, for example, a matchbook design having roughly the same amount of material. This present package is thus unique in that it locates a first fold line 24 just above the third panel 20 and at the very base ends of the devices. In doing so, the tail 38 of the item containers 34 is be folded to a hidden position when the container 10 is in a closed position, while still allowing for a free end to grip the pack when open. Upon opening, the container 10 can also force the main bodies 36 to flip out away from the first panel 16 allowing easier access for the user.

Furthermore, in accordance with the disclosed example, the container 10 may also allow the item containers 34 to fan out by altering the material fibers in the item containers 34 along the fold line 40 to alter the foldability of the material. Thus, although the item containers 34 tend to pivot away from the first panel 16 in an upright manner, the altered material isn't able to support them and the strips fan back toward the first panel 16, allowing the user greater access to the plates in the rear. As an example, the matchbook design, which does not incorporate first fold line, cannot provide these functional enhancements offered by the disclosed example.

The foregoing description is not intended to limit the scope of the invention to the precise form disclosed. It is contemplated that various changes and modifications may be made by those skilled in the art without departing from the spirit and scope of the invention.

We claim:

1. A device for storing and dispensing items comprising:
    an item container having a main body and a tail extending from the main body;
    a first panel;
    a second panel connected to the first panel along a first fold line;
    a third panel connected to the second panel along a second fold line, the second panel and the third panel defining a pocket, at least a portion of the tail being secured in the pocket, the pocket being foldable along the first fold line to a closed position in which the main body, the second and third panel, and the tail all generally overlie the first panel, the pocket being further foldable to an open position in which the third panel, the tail, and the second panel are angled away from the first panel; and
    a fourth panel foldably attached to the first panel along a third fold line, the fourth panel arranged to cover the item container, the fourth panel further being releasably attachable to the second panel to maintain the device in the closed position,
    the second panel further comprising a cut defining a flap, the fourth panel being insertable into the flap to releasably attach to the second panel.

2. The device of claim 1, wherein the second and third panels and the tail cooperate to shift the main body away from the first panel when the pocket he shifted toward the open position.

3. The device of claim 1, the first item container further comprising a plurality of frangibly connected strips, each strip being adapted to store an item.

4. The device of claim 1, further comprising a foldable blank, the blank comprising the first panel, the second panel, and the third panel.

5. The device of claim 1, further comprising a second item container similar to the first mentioned item container and having a main body and a tail, at least a portion of the tail of the second item container being disposed in and connected to the pocket, the main body of the second item container being disposed away from the main body of the first item container in the open position.

6. The device of claim 5, wherein the first item container and the second item container are arranged to overlie each other.

7. The device of claim 5, wherein the first item container and the second item container are disposed side-by-side in a common plane.

8. A device for sorting and dispensing items, comprising:
    a first item container having a main body and a tail extending from the main body;
    a first panel;
    a second panel connected to the first panel along a first fold line;
    a third panel connected to the second panel along a second fold line, the second panel and the third panel defining a pocket, at least a portion of the tail being disposed in and connected to the pocket, the pocket being foldable along the first fold line to a closed position in which the main body is disposed over the first panel and the third panel, the tail, and the second panel are disposed over the main body; and
    a fourth panel connected to the first panel along a third fold line, the fourth panel being foldable along the third fold line to a closed position in which the fourth panel is disposed over the second panel, the second panel further comprising a cut defining a flap, the fourth panel being insertable into the flap to releasably attach to the second panel.

9. The device of claim 8, the pocket being foldable to an open position in which the pocket is angled away from the first panel.

10. The device of claim 8, the first item container comprising a plurality of frangibly connected strips, each strip adapted to store an item.

11. The device of claim 8, further comprising a second item container having a main body and a tail, the tail of the second item container being secured to the second panel.

12. The device of claim 8, the first item container comprising a first sheet and a second sheet secured together.

13. The device of claim 12, the first item container further comprising a receptacle between the first sheet and the second sheet in which items may be stored.

14. The device of claim 13, the first item container further comprising a plurality of receptacles between the first sheet and the second sheet.

* * * * *

UNITED STATES PATENT AND TRADEMARK OFFICE
CERTIFICATE OF CORRECTION

| | | |
|---|---|---|
| PATENT NO. | : 7,445,142 B2 | Page 1 of 1 |
| APPLICATION NO. | : 10/863141 | |
| DATED | : November 4, 2008 | |
| INVENTOR(S) | : Ted Salani et al. | |

It is certified that error appears in the above-identified patent and that said Letters Patent is hereby corrected as shown below:

In the Claims:

At Column 6, line 3, claim 2 "he" should be -- is --.

Signed and Sealed this

Thirtieth Day of June, 2009

JOHN DOLL
*Acting Director of the United States Patent and Trademark Office*